United States Patent
Sawaya

[19]

[11] Patent Number: 5,888,493
[45] Date of Patent: Mar. 30, 1999

[54] OPHTHALMIC AQUEOUS GEL FORMULATION AND RELATED METHODS

[76] Inventor: Assad S. Sawaya, 9 Lyn La., Baiting Hollow, N.Y. 11933

[21] Appl. No.: 760,693

[22] Filed: Dec. 5, 1996

[51] Int. Cl.$^6$ .......................... A61K 31/74; A01N 25/02
[52] U.S. Cl. ...................... 424/78.04; 514/781; 514/912; 514/915
[58] Field of Search ........................ 424/78.04; 514/781, 514/912, 915

[56] References Cited

U.S. PATENT DOCUMENTS

| | | |
|---|---|---|
| 3,415,929 | 12/1968 | Lachman et al. . |
| 3,450,814 | 6/1969 | Bechtold et al . |
| 4,003,991 | 1/1977 | Krohn et al. . |
| 4,179,497 | 12/1979 | Cohen et al. . |
| 4,271,143 | 6/1981 | Schoenwald et al. . |
| 4,343,787 | 8/1982 | Katz et al. . |
| 4,349,563 | 9/1982 | Gilbert et al. . |
| 4,474,751 | 10/1984 | Haslam et al. . |
| 4,511,563 | 4/1985 | Schmolka . |
| 4,551,456 | 11/1985 | Katz et al. . |
| 4,678,855 | 7/1987 | Shepard et al. . |
| 4,767,619 | 8/1988 | Murray . |
| 4,861,755 | 8/1989 | Breipohl et al. . |
| 4,861,760 | 8/1989 | Mazuel et al. . |
| 4,883,660 | 11/1989 | Blackman et al. . |
| 5,013,545 | 5/1991 | Blackman et al. . |
| 5,137,728 | 8/1992 | Bawa et al. . |
| 5,141,928 | 8/1992 | Goldman et al. . |
| 5,164,188 | 11/1992 | Wong . |
| 5,229,128 | 7/1993 | Haddad et al. . |
| 5,252,318 | 10/1993 | Joshi et al. . |
| 5,259,998 | 11/1993 | Reich . |
| 5,292,517 | 3/1994 | Chang . |
| 5,300,295 | 4/1994 | Viegas et al. . |
| 5,318,780 | 6/1994 | Viegas et al. . |
| 5,474,764 | 12/1995 | Patel et al. ........................... 424/78.04 |
| 5,516,808 | 5/1996 | Sawaya . |

*Primary Examiner*—Carlos A. Azpuru
*Attorney, Agent, or Firm*—Darby & Darby

[57] ABSTRACT

An ophthalmic formulation is described containing at least one pharmaceutically active substance, purified water, and an amount of gelling agent effective to form an aqueous gel. The gel has a viscosity of from 75,000 to 3,000,000 centipoise and does not contain an oil phase. The pharmaceutically active substance is solubilized in the formulation. The gelling agent consists essentially of cellulose or a water soluble cellulose derivative.

33 Claims, 5 Drawing Sheets

3% Gel, Oxy-3 (150 rpm)

Fig. 5

OPHTHALMIC AQUEOUS GEL FORMULATION AND RELATED METHODS

FIELD OF THE INVENTION

The present invention is in the field of ophthalmic pharmaceutical formulations.

BACKGROUND OF THE INVENTION

In a conventional ophthalmic ointment, pharmaceutically active substances are suspended in petrolatum and mineral oil. Because the eye rejects oily fluids, however, a portion of the ointment is expelled upon application. Also, release of the active ingredient is delayed for the time required for water from the eye fluid to be exchanged with the ointment. As a result, only an inexact dose of active ingredient reaches the eye.

Furthermore, conventional ointments interfere with vision once they are applied, causing blurring. It is, for example, often required that activities of an individual be restricted until vision becomes clear after administration of an ophthalmic ointment.

While ointments exhibit some time release properties, these properties are unpredictable. The ointment is rejected in large part from the eye before a significant amount of the active ingredient is transferred to the aqueous phase.

Ophthalmic solutions suffer from similar deficiencies, as they run out of the eye upon administration. Thus, with such solutions only a low, imprecise amount of active reaches the eye. Also, solutions are generally applied to the center of the eye, where they cause blurring. For example, solutions are available for treating dry eye which contain small amounts of cellulose based additives as the active ingredient for lubricating the eye. Such products are available commercially containing 0.5% or 1% carboxymethyl cellulose and are known as "artificial tear preparations" or "lubricating eye drops". They form an occlusive film over the outer surface of the eye to protect it from drying and are used in particular to relieve dry eye associated with contact lens use. Such solutions have a low viscosity, i.e., substantially less than 10,000 cps (Brookfield LV at about 25° C.). They are applied directly to the center of the eye, i.e., to the contact lens, causing blurring. They also deliver an imprecise amount of active.

Formulations for "longer lasting" relief of dry eye are available as ointments. One such preparation is formulated from 80% white petrolatum and 20% mineral oil. Such products, however, are easily expelled from the eye and offer only relatively short term relief, i.e., not more than about 30 minutes.

Inserts are available for ophthalmic use that are formed from solid cellulose. For example, U.S. Pat. No. 5,229,128 describes rods formed of methylcellulose for insertion into the eye to treat dry eye. They are formed from powdered cellulose derivative, dried, and then preferably placed in a gelatin capsule. To administer the solid rod, the ends of the gelatin capsule are separated, the rod being kept in one segment of the capsule, the inferior cul-de-sac of the eye is withdrawn, and the rod is dropped into the lower part of the eyelid. This is a difficult procedure, and for some patients requires the assistance of a physician. If no gelatin capsule is employed, forceps must be used to administer the insert. Furthermore, the solid cellulose of the insert needs to be wetted in the eye by eye fluid. The cellulose then swells, causing a possibility of irritation from undissolved crystals in the wetted cellulose. Also, wetting of the solid cellulose to form a gel in the eye occurs in an inconsistent manner from one individual to the next. It is also difficult to incorporate additional lubricating agents in such inserts, as any additional active product may crystalize in the eye, causing possible injury.

Solid inserts which suffer from the same deficiencies are also described in U.S. Pat. No. 4,343,787.

There is therefore a need for a safe ophthalmic formulation that is not easily expelled from the eye after administration, that delivers a precise dosage, that is easy to administer, and that is capable of controlled release of a pharmaceutically active substance.

SUMMARY OF THE INVENTION

The present invention relates to a formulation adapted for ophthalmic use containing at least one pharmaceutically active substance, purified water, and an amount of gelling agent effective to form an aqueous gel. The gel has a viscosity of from 75,000 to 3,000,000 centipoise at a temperature of 22° to 30° C., preferably 25° C., and is substantially free of an oil phase. The pharmaceutically active substance is solubilized in the formulation. The gelling agent consists essentially of cellulose or a water soluble cellulose derivative. The invention also relates to a method that involves administering the formulation to the eye of an individual.

DETAILED DESCRIPTION OF THE INVENTION

The ophthalmic formulation of the invention improves over existing oil based formulations and solutions. Upon administration, aqueous eye fluids mix with the gel, resulting in immediate release of the active agent. Also, a predetermined dose reaches the site being treated. Furthermore, a much higher percentage of the dose is maintained in the eye than with a conventional ophthalmic ointment or solution.

The formulation also allows an amount of active to be applied that slowly spreads over the eye. Furthermore, it has been determined that the gel of the invention can be formulated to be substantially clear, thereby avoiding or decreasing blurring associated with conventional ophthalmic products.

In one embodiment, the invention relates to a formulation for treating dry eye. In this formulation, the cellulose, or cellulose derived, gelling agent also acts as a pharmaceutically active agent for lubricating the dry eye. There is no additional pharmaceutically active agent required, although it is possible, if desired, to add other pharmaceutically active agents, such as povidone, for either lubricating the eye or for reducing eye irritation.

The formulation of the invention provides a safe means for time release of actives into the eye. The release rate depends on the viscosity of the gel, i.e., higher viscosity results in slower release. The invention relates in particular to gels having very high viscosity and correspondingly slow release profile. In one embodiment, the gel has a viscosity of more than about 500,000 cps. More preferably, it has a viscosity of more than about 1,000,000 cps, and most preferably more than about 2,000,000 cps at about 25° C. based on Brookfield (LV) analysis. It has been determined that, for example, an aqueous gel of carboxymethyl cellulose sodium having a viscosity of about 2,500,000 releases an active in a linear manner over an extended period.

The gel of the invention is able to exhibit longer relief of, e.g., dry eye, than a conventional ointment. While, as mentioned above, a conventional ointment might offer relief of no greater than about 30 minutes, the gel of the invention, in a sufficiently viscous form, offers relief for a longer time, preferably longer than about two hours. In one embodiment, the invention releases active ingredient for more than about four hours.

Furthermore, when properly applied under the eyelid, the cellulose based gel has been found to release active ingredient over this extended period of time without interfering with vision, thereby avoiding or decreasing blurring associated with conventional ophthalmic products.

The high viscosity aqueous gel products of the invention improve over solid inserts in that they are easier and safer to administer, involving less risk of scratching the cornea. Unlike solid inserts, the gels of the present invention are substantially free of cellulose crystals that may be present in wetted solid inserts. The gels of the invention are also more comfortable than solid inserts, which can irritate the eye.

In one embodiment, the formulation contains Polymyxin B Sulfate, and Neomycin Sulfate. Most preferably it contains both. These antibiotics have been found to exhibit unexpectedly high release rates in the formulation.

The formulation of the invention can be placed in any desired dispensing device suitable for an ophthalmic formulation. The device can be an ophthalmic delivery system, such as a sterile ophthalmic tube, e.g., a conventional 3.5 g tube having an ophthalmic tip and containing the ophthalmic formulation of the invention, or a sterile single use container containing 0.2–0.5 g of the formulation.

Cellulose and its derivatives are used as gelling agents in the formulation of this invention. Most preferred is a commonly available methyl cellulose: carboxymethyl cellulose salt. Any cellulose derived gelling agent, however, that forms an aqueous gel at the desired viscosity, i.e., is soluble in water and forms a gel, can be used. Such derivatives are well known, as are their properties, and are described, e.g., in the U.S. Pharmacopeia (1995) (UNITED STATES PHARMACOPEIAL CONVENTION, INC., THE UNITED STATES PHARMACOPEIA/THE NATIONAL FORMULARY (1995)). Such gelling agents include, but are not limited to, methyl cellulose, hydroxypropyl cellulose, methyl hydroxypropyl cellulose, hydroxypropyl methyl cellulose, cellulose acetate, ethyl cellulose, methyl hydroxyethyl cellulose, hydroxyethyl cellulose, and cellulose gum. Cellulose based gelling agents are advantageous over, for example, cross-linked acrylic polymers. For example, Carbopol™, a cross-linked acrylic polymer, has been used to form an aqueous gel containing pilocarpine hydrochloride for ophthalmic use. Cellulose based gelling agents, however, are less likely to cause adverse reactions.

In the aqueous gel for ophthalmic use, the amount of cellulose used varies depending on the type of agent. High viscosity cellulose based agents are preferred. Such agents have a higher number of substituents, such as methoxy, ethoxy, hydroxy propyl and carboxy substituents, attached to the cellulose backbone than low viscosity cellulose based agents. High viscosity carboxymethyl cellulose sodium in an amount of from about 1.5 to 5 wt. % is preferred, and from about 2 to 5 wt. % is more preferred. If desired, however, a low viscosity cellulose based gelling agent may be used in a higher concentration than when using the high viscosity cellulose, constituting even 10 wt. % or more of the formulation.

Suitable cellulose based preparations for use in the invention are commonly commercially available. For example, commercial sources of high viscosity carboxymethyl cellulose sodium that are suitable for making a high viscosity cellulose based ophthalmic gel according to the invention include Ruger Chemical Co., Akzo Chemicals Inc., Dow Chemical Co., Miles Inc., Amend Drug and Chemical, Inc., and Aqualon Co.

The formulation may contain additional pharmaceutically inactive substances. For example, it may contain one or more solubilizing agents, such as polysorbate 20, polysorbate 40, polysorbate 60 or polysorbate 80. The formulation may also contain a dispersant, such as lecithin or glycerine. Collagen can also be added. Other additives include cyclodextrins, in particular alpha, beta, and gamma cyclodextrins. Also, vitamin E, particularly in a solubilized form, or other antioxidants, including butylate hydroxyanisole (BHA) and butylate hydroxytoluene (BHT), may be added. Some additional examples of inactives follow, including in some cases typical amounts for an ophthalmic formulation: benzalkonium chloride (0.01%), boric acid (0.1–0.1%), sodium carbonate (1.0%), potassium chloride (0.2%), propylene glycol, polyoxyethylene, polyoxypropylene, cetyl alcohol, glyceryl monostereate, polyoxyl 40 stearate, glycerin (1%), polyvinyl alcohol (1.4%), poloxamer 188, sodium citrate, sodium thiosulfate (0.3%), sodium bisulfite, dextran 70 (0.1%), tyloxagol (0.25%), acetic acid, polyethylene glycol 300, povidone, gelatin A (0.01%), dextrose, magnesium chloride, alginic acid, and sodium borate. The optimal amount of inactive ingredient employed in the formulation can be conventionally determined based on the particular active pharmaceutical, and the intended use.

Preferred amounts of antibiotics are Polymyxin B Sulfate (5,000–10,000 units/gm) Neomycin Sulfate (1.75–3.5 mg/gm). Other antibiotics, in their preferred amounts, include Gramicidin (0.025 mg/gm), Zinc Bacitracin (400–500 units/gm), Gentamicin (0.3%); Chloramphenicol (0.5%), Tobramycin (0.3%), Erythromycin, (5 mg/gm), and Tetracycline HCl (1%).

The formulation may include a steroid. Examples of such steroids, and preferred amounts, include Hydrocortisone (1%), Prednisone (0.1%), Fluorometholone acetate (0.1%), Dexamethasone Sodium Phosphate (0.05%), Dexamethasone (0.1%), Suprofen (1%), Fluorometholone (0.1%–0.25%), and Medrysone (1.0%).

Commercially available pharmaceutically active drugs for use in the aqueous gel of the invention, include, without limitation (the preferred concentrations being indicated in parentheses following each ingredient), Proparacaine hydrochloride (0.5%), Betaxolol hydrochloride (0.5%, Cyclopentolate hydrochloride (0.5%–2%), Phenylephrine hydrochloride (1%–10%), Epinephrine (1.0%–2.0%), Apraclonidine hydrochloride (1%), Atropine sulfate (0.5%–1.0%), Carbachol (0.75%–3.0%), Pilocarpine hydrochloride (0.25%, 0.5%, 1%, 2%, 3%, 4%, 5%, 6%, 8%, and 10%), Sulfacetamide Sodium (10%), Homatropine Hydrobromide (2.0%–5.0%), Scopolamine Hydrobromide (0.25%), Tropicamide (0.5%–1.0%), Naphazolinehydrochloride (0.1%), Tetrahydrozoline Hydrochloride (0.05%), Oxymetazoline Hydrochloride (0.025%), Ketorolac Tromethamine (0.5%), Levobunolol hydrochloride (0.25%–0.5%), Idoxuridine (0.1%), Trimethoprim (1 mg/gm), Dipivefrin hydrochloride (0.1%), Metipranolol (0.3%), Trifluridine (1%), Diclofenac Sodium (0.1%), Zinc Isoflurophate (0.25%), Demecarium Bromide (0.125%–0.25%), Timolol Maleate (0.25%–0.5%), Carteolol hydrochloride (10 mg/gm), Vidrabine (3%), glycerin and Dextran 70 (0.1%).

Examples of antibiotic combinations in the ophthalmic delivery system of the invention are shown below.

| A) | Polymyxin B Sulfate | 10,000 units |
| | Neomycin Sulfate | 3.5 mg (as base) |
| | Zinc Bacitracin | 400 units |
| B) | Polymyxin B Sulfate | 10,000 units |
| | Zinc Bacitracin | 500 units |
| C) | Polymyxin B Sulfate | 10,000 units |
| | Neomycin Sulfate | 1.75 mg (as base) |
| | Gramicidin | 0.025 mg |
| D) | Polymyxin B Sulfate | 10,000 units |
| | Neomycin Sulfate | 3.5 mg (as base) |
| | Zinc Bacitracin | 400 units |
| | Hydrocortisone | 1% |
| E) | Polymyxin B Sulfate | 10,000 units |
| | Neomycin Sulfate | 3.5 mg (as base) |
| | Hydrocortisone | 1% |
| F) | Polymyxin B Sulfate | 10,000 units |
| | Neomycin Sulfate | 3.5 mg |
| | Dexamethasone | 0.1% |
| G) | Polymyxin B Sulfate | 10,000 units |
| | Neomycin Sulfate | 3.5 mg |
| | Prednisolone Acetate | 0.5% |

The invention is illustrated by the following examples.

EXAMPLE 1

A lubricating gel for treating dry eyes according to the present invention was prepared as follows.

938.47 grams of Purified Water at 80° C.±2° C. was placed in a 1 gallon capacity stainless steel kettle, equipped with double motion mixing device. While mixing, the following ingredients were added in the order given, ensuring that each ingredient was completely dissolved before adding the next. The temperature was maintained at 70° C.

| Purified Water | 938.47 grams |
| Sodium Chloride | 4.90 grams |
| Potassium Chloride | 0.750 grams |
| Calcium Chloride | 0.480 grams |
| Magnesium Chloride | 0.300 grams |
| Sodium Citrate | 5.600 grams |
| Povidone | 1.00 grams |
| Glycerine | 2.00 grams |
| Sodium Hydroxide | 1.50 grams |
| (0.5 Normal Solution) | |

Mixing was continued for 5–10 minutes after the ingredients were added. Continuing to mix the ingredients, the temperature was raised to 90° C.±5° C., and 45 grams of high viscosity carboxymethyl cellulose sodium slowly sprinkled in. Mixing was continued until all of the carboxymethyl cellulose sodium was completely dissolved. Maintaining the same temperature, the entire contents of the batch was transferred into a presterilized vacuum tank. The tank was closed, and a vacuum pulled to 5 inches Hg while mixing. The temperature of the batch was then raised to 121° C. for 45 minutes to sterilize the mixture. Continuing to mix, the temperature was slowly lowered to 40° C.±2° C. Mixing was stopped and the temperature lowered to 30° C.±2° C.

EXAMPLE 2

An aqueous gel of 0.025% oxymetazoline HCl was prepared containing Parts A and B as follows:

| Part A | |
| --- | --- |
| Purified Water | 200 grams |
| Boric Acid | 9.6 grams |
| Sodium Borate | 0.13 grams |
| Edetate Disodium | 1.0 grams |
| Benzalkonium Chloride | 0.1 grams |
| Oxymetazoline HCl | 0.26 grams |
| Sodium Chloride | 4.0 grams |
| Part B | |
| Purified Water | 750 grams |
| Hydroxypropyl Methyl Cellulose | 35 grams |

Part A: All ingredients in Part A were mixed and dissolved, in the order listed, until a clear solution was obtained. The solution was then sterilized by membrane filtration (0.2 microns).

Part B: Purified water was heated to 90° C. Hydroxypropyl methyl cellulose was added and mixed until it was uniformly dispersed. While mixing in a pressure vessel, the mixture was sterilized at 121° C. for 30–45 minutes.

The temperature was brought down to 50°–55° C. Part A was then aseptically added. Mixing was continued, and the temperature lowered to 25°–30° C. A gel resulted that was used to aseptically fill pre-sterilized 3.5 gram ophthalmic tubes.

EXAMPLE 3

The ophthalmic oxymetazoline HCl preparation made in Example 2 was administered as follows. (To avoid contamination, the tip of the container was not touched to any surface and the cap replaced after using.) The lower lid of the eye administered to was pulled down and a small amount of gel applied (approximately one quarter inch (¼")) to the inside of the eyelid. The weight of the ¼ inch ribbon was about 20 mg.

On two separate days, 1 week apart, the gel was administered as above. The first day, the gel was administered to the left eye, the second to the right eye. In both cases, the gel was not expelled. There was a slight feeling of pressure around the lid area where the gel was applied. Within minutes, the treated eye turned white as compared with the untreated eye. After application of the gel, slight pressure discomfort seemed to lessen. After 30–45 minutes, no pressure was felt. The difference in color between the eyes remained for 2–4 hours.

EXAMPLE 4

The potency of antibiotic preparations can be demonstrated by measuring their inhibitory effects on selected micro-organisms under controlled conditions. Procedures for doing this are found in The United States Pharmacopeia (UNITED STATES PHARMACOPEIAL CONVENTION, INC., THE UNITED STATES PHARMACOPEIA/THE NATIONAL FORMULARY (1995) p.1690). The same methods may be used to compare, quantitatively, the ability of different formulation bases to release antibiotics to areas they are applied to. The preparation which diffuses the most antibiotic is considered to be the most effective. This procedure was used to compare antibiotics in an aqueous gel formulation with conventional antibiotic ointment formulations.

Procedure

Assay plates were prepared containing two layer of media (a base layer and a seed layer) designed to promote the rapid growth of selected micro-organisms. The media were liquified, inoculated with a purified culture, poured into petri-dishes and allowed to solidify. A stainless steel cylinder was then placed in the middle of the plate, with one of its open faces flush against the medium. The cylinders were filled with the product to be tested and placed in an incubator. After 24 hours the plates were removed from the incubator and observed.

On each plate a circular zone surrounding the cylinder was formed where no microbial growth was observed. This zone is formed as the antibiotic diffuses out of the formulation base in the cylinder and into the inoculated media. The diffusing antibiotic spreads outward, inhibiting the growth of micro-organisms. The greater the amount of antibiotic released from the preparation, the larger the zone formed. Diffusion effectiveness may be observed by comparing zone diameter measurements.

The diffusion effectiveness of three different antibiotics (Neomycin Sulfate, Polymyxin B Sulfate and Bacitracin Zinc) was evaluated for both the aqueous gel formulation of this invention and a conventional triple antibiotic ointment. Each formulation contained the same potency of antibiotic.

Results

Results were as follows:

| Antibiotic | Base Form | Potency | Zone Diameter Test 1 | Test 2 |
| --- | --- | --- | --- | --- |
| Zinc Bacitracin | Ointment | 400 IU/gm | 19.2 mm | 22.2 mm |
|  | Gel | " | 29.3 mm | 28.0 mm |
| Polymyxin B Sulfate | Ointment | 10,000 IU/gm | 15.4 mm | 18.6 mm |
|  | Gel | " | 26.4 mm | 26.8 mm |
| Neomycin Sulfate | Ointment | 3.5 mg base/gm | 18.2 mm | 19.8 mm |
|  | Gel | " | 25.2 mm | 28.6 mm |

Observations and Conclusions

In all cases, the zone diameter of the antibiotic in the aqueous gel base was significantly greater than that of the corresponding ointment base. The relative amount of antibiotic delivered into the medium from each formulation type was determined by a comparison of the areas of the individual zones. This calculation showed that the gel base Zinc Bacitracin formula delivered at least 59% more antibiotic than the traditional ointment, that Polymyxin B Sulfate delivered at least 108% more, and Neomycin Sulfate delivered at least 92% more.

EXAMPLE 5

Release rates of antibiotic from the gel formulation of the invention were compared with those of a conventional oil based formulation. The procedure of Example 4 was followed. The units/gram released were calculated from zone size.

Following are results obtained for three microorganisms tested.

A. *Bordetella Bronchiseptica.*

Release of Polymyxin B Sulfate from the base formulation was measured in the amounts shown.

| Run | Triple Ointment Units/Gram | Triple Gel Units/Gram |
| --- | --- | --- |
| 1 | 11.5 | 332.1 |
| 2 | 4.7 | 496.6 |
| 3 | 10.1 | 987.0 |
| Average | 8.76 | 602.2 |
| 602.2/8.76 = 68.74 times greater release rate | | |

B. *Micrococcus Luteus*

Release of Zinc Bacitracin from the base formulation was measured in the amounts shown.

| Run | Triple Ointment Units/Gram | Triple Gel Units/Gram |
| --- | --- | --- |
| 1 | 0.4 | 22.9 |
| Average | 0.4 | 22.9 |
| 22.9/0.4 = 57.25 times greater release rate | | |

C. *Staphylococcus Epidermis*

Release of Neomycin from the base formulation was measured in the amounts shown.

| Run | Triple Ointment mg/gm | Triple Gel mg/gm |
| --- | --- | --- |
| 1 | 0.0013 | 0.015 |
| 2 | 0.0037 | 0.019 |
| Average | 0.0025 | 0.016 |
| 0.01675 = 6.7 times greater release rate | | |

These results show a higher release rate for the antibiotics in the aqueous gel formulation of the invention than for a corresponding ointment. The release rates for Polymyxin B Sulfate and Zinc Bacitracin were much higher than expected, i.e., 69 and 57 times the ointment release rate, respectively.

EXAMPLE 6

Carboxymethyl cellulose sodium having high viscosity, was used in the preparation of the following gels as follows.

1.0% of high viscosity carboxymethyl cellulose sodium (Amend Drug and Chemical, Inc. Irvington, N.J.) was dissolved in 97.797% (80° C.) purified water, while continuously mixing and maintaining a temperature of 800° C. While mixing, the following ingredients were added:

| Sodium chloride | 0.49% |
| --- | --- |
| Potassium chloride | 0.075% |
| Calcium chloride | 0.048% |
| Magnesium chloride | 0.03% |
| Sodium acetate | 0.39% |
| Sodium citrate | 0.17% |

The final mixture, Formula "A", had a pH of 7.4 and was an optically clear gel having a viscosity of 7350 centipoise.

2.0% of high viscosity carboxymethyl cellulose sodium was dissolved in 96.79% (80° C.) purified water while continuously mixing and maintaining a temperature of 80° C. While mixing, the salts listed for formula "A" were added. The final pH of the mixture, formula "B" was 7.4, forming an optically clear gel having a viscosity of 706680 centipoise.

3.0% of high viscosity carboxymethyl cellulose sodium was dissolved in 95.797% (80° C.) purified water while continuously mixing and maintaining a temperature of 80° C. While mixing the salts listed for formula "A" were added. The final pH of the mixture was 7.4, forming an optically clear gel having a viscosity of about 1,500,000 centipoise.

4.0% of high viscosity carboxymethyl cellulose sodium was dissolved in 94.797% (80° C.) purified water while continuously mixing and maintaining a temperature of 80° C. While mixing the salts listed for formula "A" were added. The final pH of the mixture was 7.4, forming an optically clear gel having a viscosity of about 2,286,000 centipoise.

PROCEDURE FOR OPHTHALMIC GEL DISSOLUTION

A modified dissolution test apparatus was used to measure the time needed to dissolve ophthalmic gels. Ophthalmic gels were tested in the balanced salt solution described above at pH 7.4 and a temperature of 37° C.

The apparatus (vessel) used was cylindrical, 7.0 cm in diameter, 14.5 cm high and had a minimal capacity of 473 ml. A speed regulating device was used to rotate a magnetic mixer at 60 RPM or 150 RPM.

7.5 grams of each sample was mixed with 0.04 grams of crystal violet solution to allow observation of gel dissolution, and placed into the dissolution vessel containing 375 ml of balanced salt solution. The vessel was maintained at 37° C. and the solution mixed. The time required for the gel to completely dissolve in the fluid was recorded.

PROCEDURE FOR VISCOSITY MEASUREMENT

A Brookfield Digital Viscometer (Model DV-1 (DVM)) was used, equipped with a helipath stand and an LV attachment. The viscosities of 90 g samples of various gels were measured using a 100 cc cylindrical container at room temperature. Gels with viscosities of 1,000,000 to less than 2,000,000 cps were tested with a TF spindle at 0.3 RPM. Gels with viscosities of 600,000 to less than 1,000,000 cps were tested with a TE spindle at 0.3 RPM. Gels with viscosities of 5,000 to less than 600,000 cps were tested with a TD spindle at various RPMs.

GEL DISSOLUTION TEST

The results for the viscosity measurements are shown in the Table below. As can be seen from the Table and FIG. 1, the gel of the invention dissolved in balanced salt solution at a rate which was dependent on the viscosity of the preparation. Thus, the higher the viscosity, the longer the dissolution time. Also, the relationship between gel viscosity and dissolution time was linear.

Figure 1:
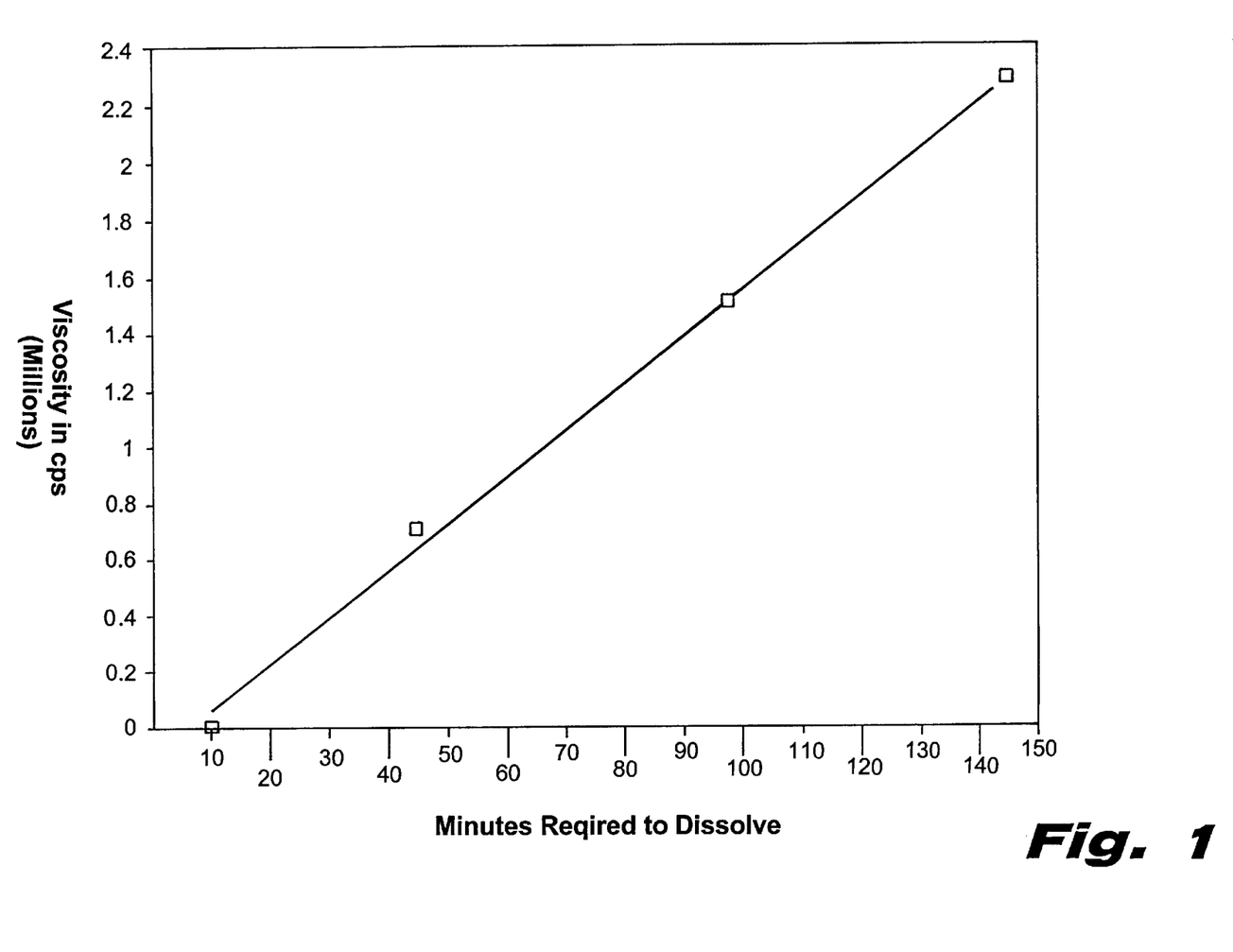
FIG. 1 is a graph showing the dissolution time for aqueous gels made from high viscosity carboxymethyl cellulose sodium and having varying viscosities.

| Form. | % CMC* | Viscosity | Time to Dissolve |
| --- | --- | --- | --- |
| A | 1% | 7350 cps | 10 minutes |
| B | 2% | 706680 cps | 45 minutes |
| C | 3% | 1,500,000 cps | 97 minutes |
| D | 4% | 2,286,000 cps | 145 minutes |

*CMC = carboxymethyl cellulose sodium

OXYMETAZOLINE HCL GEL-DISSOLUTION TEST

The modified dissolution test apparatus described above was used to measure the time needed for dissolution of oxymetazoline HCl in various ophthalmic gel preparations. Three formulations were tested. All contained 0.025% oxymetazoline HCl, but different amounts of high viscosity carboxymethyl cellulose sodium (cmc). Specifically, "Oxy-1" contained 1% cmc, "Oxy-3" contained 3% cmc, and "Oxy-4.5" contained 4.5% cmc. Oxy- 1 had a viscosity of less than 10,000 cps, Oxy-3 had a viscosity of about 1,500,000 cps and Oxy-4.5 had a viscosity of greater than 2,000,000 cps.

7.5 grams of each oxymetazoline gel preparation was added to 375 ml of the balanced salt solution shown below.

| BALANCED SALT SOLUTION | |
| --- | --- |
| Sodium chloride | 0.64% |
| Potassium chloride | 0.075% |
| Calcium chloride | 0.048% |
| Magnesium chloride | 0.03% |
| Sodium acetate | 0.39% |
| Sodium citrate | 0.17% |
| Purified water | 98.647% |

The final formulation of the Oxy-1 sample was as follows:

| OXY-1 FORMULATION OXYMETAZOLINE HCL 0.025% IN 1% CMC SODIUM | |
| --- | --- |
| | w/w Basis |
| Purified water | 97.662% |
| Sodium chloride | 0.20% |
| Potassium chloride | 0.075% |
| Calcium chloride | 0.048% |
| Magnesium chloride | 0.03% |
| Sodium citrate | 0.56% |
| Povidone | 0.10% |
| Glycerine | 0.20% |
| Dextran 70 | 0.10% |
| Oxymetazoline HCl | 0.025% |
| Carboxymethyl cellulose sodium (high viscosity) | 1.00% |

The Oxy-3 and Oxy-4.5 formulations were the same but containing more cmc and a correspondingly lower amount of water. All of the gels were optically clear and had a pH of 7.4.

The time release profile for each was then measured. Oxymetazoline HCl was assayed using a standardized HPLC method (US Pharmacopeia 1995). At various time intervals, samples taken from the dissolution test apparatus were injected into the HPLC instrument. A standard sample of oxymetazoline HCl was also injected into the instrument. Results for the test samples were calculated as a percent of the theoretical amount.

The results are shown in the Tables below and in FIGS. 2–5. The dissolution test at 60 RPM indicated that the oxymetazoline HCl in OXY-1 was completely released in less than 15 minutes, corresponding to a calculated release rate of 8% per minute. 80% of the oxymetazoline HCl in Oxy-3 was released in 95 minutes, corresponding to a calculated release rate of 0.84% per minute. 80% of the oxymetazoline HCl in OXY-4.5 was released in 239 minutes, corresponding to a calculated release rate of 0.33% per minute.

Figure 4:
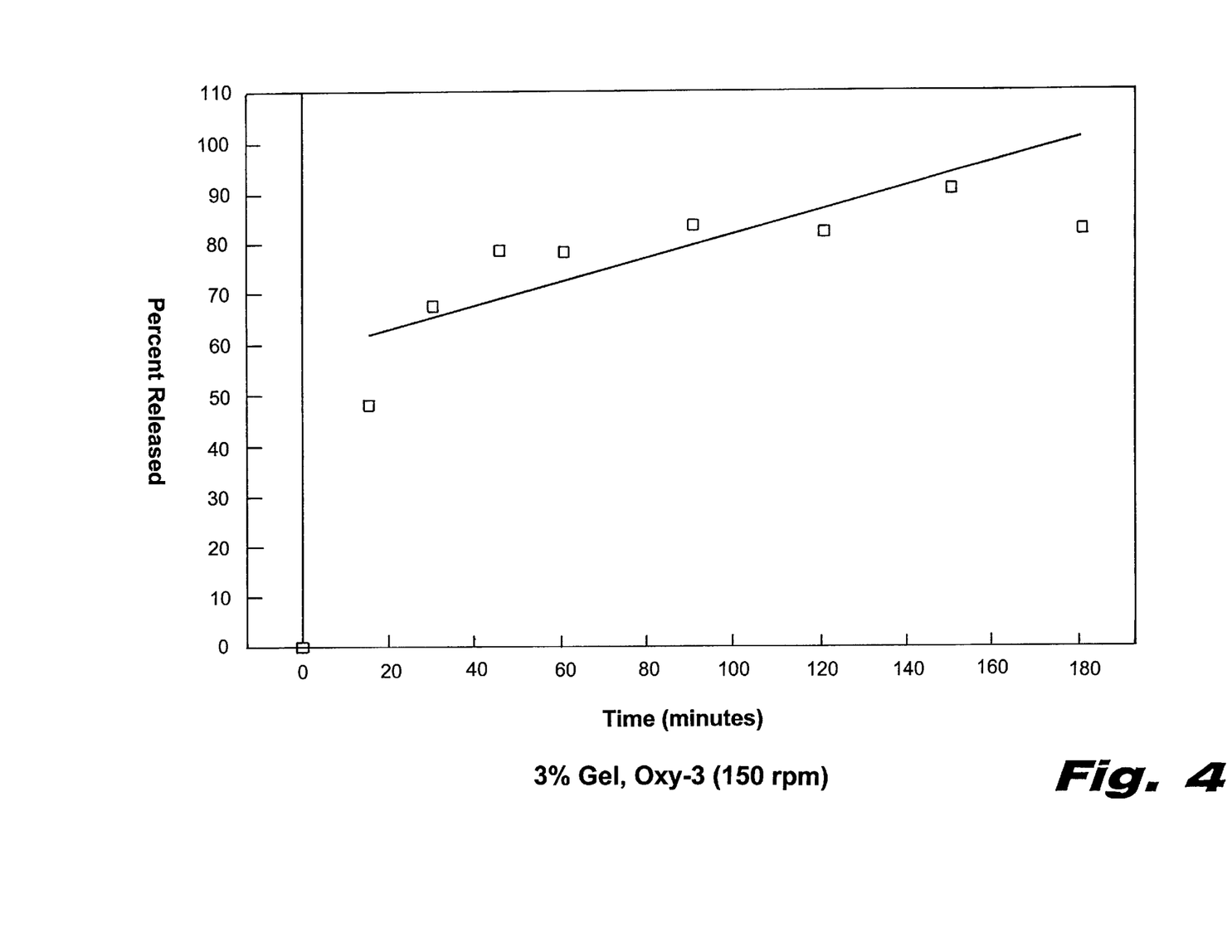
FIGS. 4 and 5 are graphs showing the percent of oxymetazoline HCl released over time from two high viscosity aqueous gels of the invention made with 3.0% and 4.5% high viscosity carboxymethyl cellulose sodium (Oxy-3 and Oxy-4.5) in a dissolution test at 150 RPM.
Figure 5:
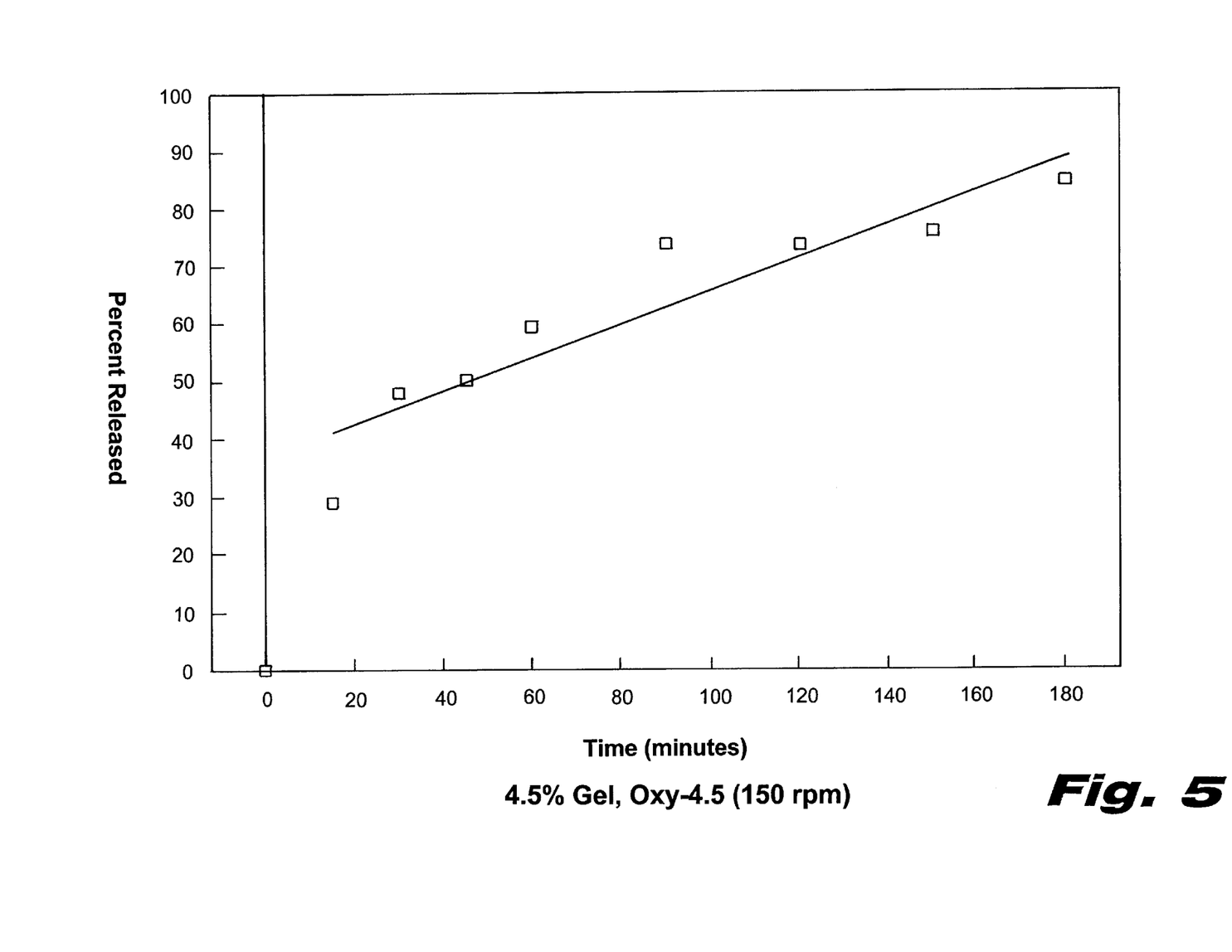

The dissolution tests at 150 RPM indicate that the oxymetazoline HCl in OXY-1 was completely released in less than 15 minutes, corresponding to a calculated release rate of 8% per minute. 80% of the oxymetazoline HCl in Oxy-3 was released in 82 minutes, corresponding to a calculated release rate of 0.975% per minute. 74% of the oxymetazoline HCl in OXY-4.5 was released in 150 minutes, corresponding to a calculated release rate of 0.49% per minute.

Figure 2:
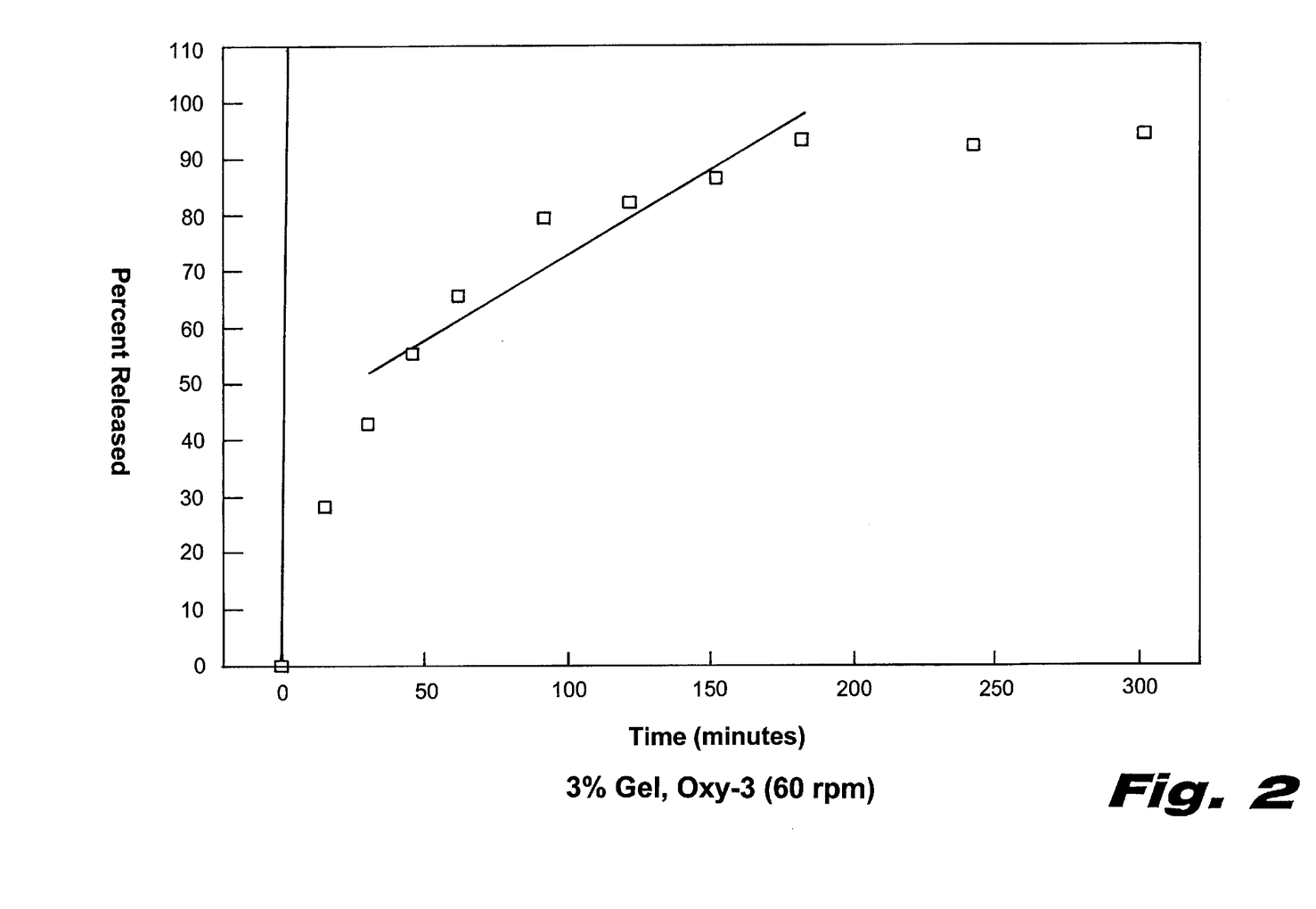
FIGS. 2 and 3 are graphs showing the percent of oxymetazoline HCl released over time from two high viscosity aqueous gels of the invention made with 3.0% and 4.5% high viscosity carboxymethyl cellulose sodium (Oxy-3 and Oxy-4.5) in a dissolution test at 60 RPM.
Figure 3:
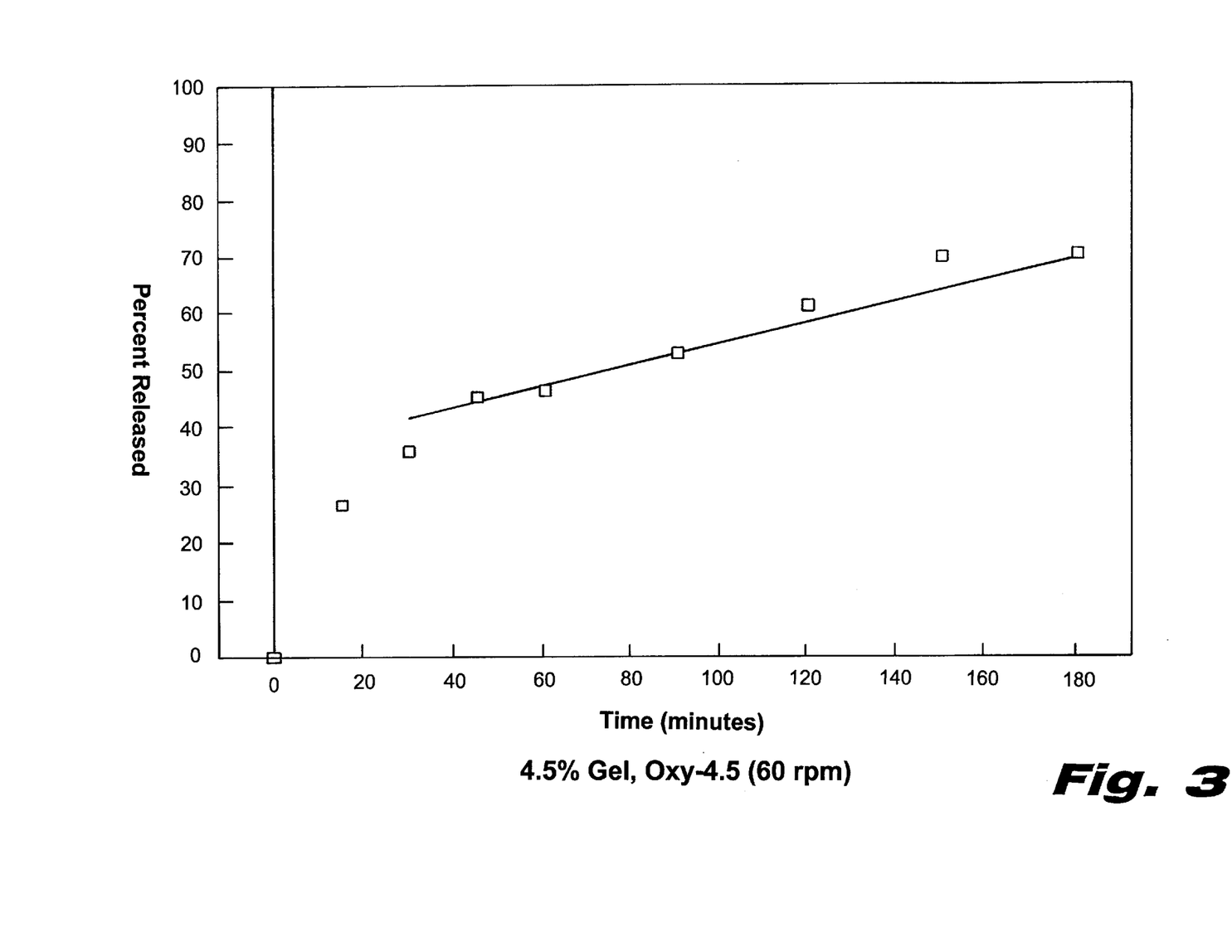

DISSOLUTION CONDUCTED AT 60 RPM AT 37° C.
USING BALANCED SALT SOLUTION, PH 7.4
Percent of 0.025% oxymetazoline HCl gel released

| TIME IN MINUTES | OXY-1 | OXY-3 | OXY-4.5 |
|---|---|---|---|
| 0 | — | — | — |
| 5 | 94.6 | — | — |
| 15 | 88.0 | 28.3 | 26.6 |
| 30 | — | 43.0 | 35.7 |
| 45 | — | 55.5 | 45.2 |
| 60 | — | 65.7 | 46.4 |
| 120 | — | 82.2 | 60.8 |
| 180 | — | 93.4 | 70.5 |
| 240 | — | — | 88.1 |

DISSOLUTION CONDUCTED AT 150 RPM AT 37° C.
USING BALANCED SALT SOLUTION, PH 7.4
Percent of 0.025% oxymetazoline HCl gel released

| TIME IN MINUTES | OXY-1 | OXY-3 | OXY-4.5 |
|---|---|---|---|
| 0 | — | — | — |
| 5 | — | — | — |
| 15 | 100.8 | 48.0 | 29 |
| 30 | 94.7 | 67.8 | 48 |
| 45 | — | 78.6 | 50.1 |
| 60 | — | 78.4 | 59.3 |
| 120 | — | 82.7 | 73.5 |
| 150 | — | 91.4 | 75.5 |
| 180 | — | — | 84.5 |

OXYMETAZOLINE HCL GEL

The results described above are summarized in the Table below.
Summation of Results

| GEL | GEL VISCOSITY IN CPS | DISSOLUTION SPEED (RPM) | TIME REQUIRED TO DISSOLVE 80% OF OXY-HCL (MINUTES) | CALCULATED DISSOLUTION RATE (PERCENT PER MINUTE) |
|---|---|---|---|---|
| Oxy-1 | Less than 10,000 | 60 | 10 | 8.0 |
| Oxy-1 | Less than 10,000 | 150 | 10 | 8.0 |
| Oxy-3 | 1,500,00 (approx.) | 60 | 95 | 0.84 |
| Oxy-3 | 1,500,000 (approx.) | 150 | 82 | 0.975 |
| Oxy-4.5 | >2,000,000 (approx.) | 60 | 239 | 0.33 |
| Oxy-4.5 | >2,000,000 (approx.) | 150 | 150 (74% dissolved) | 0.49 |

Thus, the high viscosity ophthalmic gels prepared from carboxymethyl cellulose sodium had a prolonged dissolution rate as the viscosity of the gels increased. Furthermore, oxymetazoline HCl formulated in these gels had a prolonged dissolution rate as the viscosity of the gels increased. In addition, the relationship between viscosity and dissolution time was linear between about 20 and 85% release of the active ingredient. Thus, the aqueous high viscosity cellulose based gel of the invention can advantageously be used as an effective, safe, ophthalmic formulation with control release properties.

I claim:

1. An ophthalmic aqueous gel formulation comprising a pharmaceutically active substance in a therapeutically effective amount for those in need thereof, purified water, and an amount of a gelling agent effective to form an aqueous gel, said formulation being substantially free of an oil phase, said gel having a Brookfield LV viscosity of from about 75,000 to about 3,000,000 cps at a temperature of from 22° to 30° C., said pharmaceutically active substance being solubilized in said formulation, wherein said gelling agent consists essentially of cellulose or a water soluble cellulose derivative.

2. A formulation according to claim 1 wherein said cellulose derivative is soluble in said aqueous formulation at a viscosity of about 75,000 cps at 22° to 30° C.

3. A formulation according to claim 1 wherein said cellulose derivative is soluble in said aqueous formulation at a viscosity of about 2,500,000 cps at 22 to 30° C.

4. A formulation according to claim 1 wherein said gel has a viscosity of less than about 300,000 cps.

5. An ophthalmic delivery system containing the formulation of claim 1.

6. An ophthalmic delivery system of claim 5 comprising a sterile ophthalmic tube having an ophthalmic tip and containing said aqueous gel.

7. A formulation according to claim 1 wherein said gelling agent is selected from the group consisting of methyl cellulose, hydroxypropyl cellulose, methyl hydroxypropyl cellulose, hydroxypropyl methyl cellulose, cellulose acetate, ethyl cellulose, methyl hydroxyethyl cellulose, hydroxyethyl cellulose, and cellulose gum.

8. A formulation according to claim 1 wherein said gelling agent is carboxymethyl cellulose salt.

9. A formulation according to claim 1 wherein said active substance is Polymyxin B Sulfate.

10. A method comprising administering the formulation of claim 1 to the eye of an individual.

11. An ophthalmic aqueous gel formulation for treating dry eye comprising purified water and an amount of an agent effective to form an aqueous gel and to lubricate dry eye, said formulation being substantially free of an oil phase, said gel having a Brookfield LV viscosity of from about 75,000 to about 3,000,000 cps at a temperature of from 22° to 30° C., wherein said agent effective to form an aqueous gel consists essentially of cellulose or a cellulose derivative that is water soluble at said viscosity.

12. A formulation according to claim 11 wherein said cellulose derivative is soluble in said aqueous formulation at a viscosity of 75,000 cps at 22° to 30° C.

13. A formulation according to claim 11 wherein said cellulose derivative is soluble in said aqueous formulation at a viscosity of 2,500,000 cps at 22° to 30° C.

14. A formulation according to claim 11 wherein said gel has a viscosity of less than 300,000 cps.

15. A formulation according to claim 11 having a viscosity of more than about 500,000 cps.

16. A formulation according to claim 11 having a viscosity of more than about 1,000,000 cps.

17. An ophthalmic delivery system containing the formulation of claim 11.

18. An ophthalmic delivery system of claim 17 comprising a sterile ophthalmic tube having an ophthalmic tip and containing said aqueous gel.

19. A formulation according to claim 11 wherein said gelling agent is selected from the group consisting of methyl cellulose, hydroxypropyl cellulose, methyl hydroxypropyl cellulose, hydroxypropyl methyl cellulose, cellulose acetate, ethyl cellulose, methyl hydroxyethyl cellulose, hydroxyethyl cellulose, and cellulose gum.

20. A formulation according to claim 11 wherein said gelling agent is carboxymethyl cellulose salt.

21. An ophthalmic aqueous gel formulation comprising a pharmaceutically active substance in a therapeutically effective amount for those in need thereof, purified water, and an amount of a gelling agent effective to form an aqueous gel, said formulation being substantially free of an oil phase, said gel having a Brookfield LV viscosity of from about 500,000 to about 3,000,000 cps at a temperature of from 22° to 30° C., said pharmaceutically active substance being solubilized in said formulation, wherein said gelling agent consists essentially of cellulose or a water soluble cellulose derivative.

22. A formulation according to claim 21 wherein said cellulose derivative is soluble at a Brookfield LV viscosity of 2,500,000 cps at 22° to 30° C.

23. A formulation according to claim 21 having a Brookfield LV viscosity of greater than 1,000,000 cps.

24. A formulation according to claim 21 having a Brookfield LV viscosity of greater than 2,000,000 cps.

25. An ophthalmic delivery system containing the formulation of claim 21.

26. An ophthalmic delivery system of claim 21 comprising a sterile ophthalmic tube having an ophthalmic tip and containing said aqueous gel.

27. A formulation according to claim 21 wherein said gelling agent is selected from the group consisting of methyl cellulose, hydroxypropyl cellulose, methyl hydroxypropyl cellulose, hydroxypropyl methyl cellulose, cellulose acetate, ethyl cellulose, methyl hydroxyethyl cellulose, hydroxyethyl cellulose, and cellulose gum.

28. A formulation according to claim 21 wherein said gelling agent is carboxymethyl cellulose salt.

29. A method comprising administering the formulation of claim 21 to the eye of an individual.

30. An ophthalmic aqueous gel formulation comprising a pharmaceutically active substance in a therapeutically effective amount for those in need thereof, purified water, an amount of a gelling agent effective to form an aqueous gel, said formulation being substantially free of an oil phase, said gel having a Brookfield LV viscosity of from about 2,000,000 to 3,000,000 cps at a temperature of from 22° to 30° C., said pharmaceutically active substance being solubilized in said formulation, wherein said gelling agent consists essentially of carboxymethyl cellulose salt.

31. An ophthalmic aqueous gel formulation according to claim 30 for treating dry eye wherein said gelling agent is also said pharmaceutically active substance.

32. An ophthalmic aqueous gel formulation according to claim 30 wherein said viscosity is at a temperature of 25° C.

33. An ophthalmic aqueous gel formulation according to claim 30 wherein said gelling agent is carboxymethyl cellulose sodium.

\* \* \* \* \*